US009493821B2

(12) United States Patent
Du et al.

(10) Patent No.: US 9,493,821 B2
(45) Date of Patent: Nov. 15, 2016

(54) DNA LIBRARY, PREPARATION METHOD THEREOF, AND DEVICE FOR DETECTING SNPS

(75) Inventors: Ye Du, Shenzhen (CN); Meiru Zhao, Shenzhen (CN); Ying Chen, Shenzhen (CN); Jinghua Wu, Shenzhen (CN); Geng Tian, Shenzhen (CN); Jun Wang, Shenzhen (CN)

(73) Assignee: BGI TECH SOLUTIONS CO., LTD., Shenzhen (CN)

(*) Notice: Subject to any disclaimer, the term of this patent is extended or adjusted under 35 U.S.C. 154(b) by 0 days.

(21) Appl. No.: 13/989,031

(22) PCT Filed: Sep. 21, 2011

(86) PCT No.: PCT/CN2011/079971
§ 371 (c)(1),
(2), (4) Date: Jul. 8, 2013

(87) PCT Pub. No.: WO2012/068919
PCT Pub. Date: May 31, 2012

(65) Prior Publication Data
US 2013/0288907 A1     Oct. 31, 2013

(30) Foreign Application Priority Data

Nov. 23, 2010    (CN) .......................... 2010 1 0555192

(51) Int. Cl.
*C12Q 1/68* (2006.01)
*C12N 15/10* (2006.01)
*C40B 50/06* (2006.01)

(52) U.S. Cl.
CPC ........... *C12Q 1/683* (2013.01); *C12N 15/1093* (2013.01); *C12Q 1/6869* (2013.01); *C12Q 1/6883* (2013.01); *C40B 50/06* (2013.01); *C12Q 2521/313* (2013.01); *C12Q 2525/191* (2013.01)

(58) Field of Classification Search
CPC .................................. C12Q 1/683; C12Q 1/68
USPC .......................................................... 506/2
See application file for complete search history.

(56) References Cited

U.S. PATENT DOCUMENTS 7,985,547 B2 * 7/2011 Sapolsky et al. ........ C12Q 1/68
                                                                    435/6

FOREIGN PATENT DOCUMENTS

| CN | 1341750 A | 3/2002 |
|---|---|---|
| CN | 101230490 A | 7/2008 |
| CN | 101343667 A | 1/2009 |
| CN | 101845489 A | 9/2010 |
| CN | 102061526 A | 5/2011 |
| EP | 2248914 A1 | 11/2010 |
| KR | 20090033307 A | 4/2009 |
| WO | 2009126395 A1 | 10/2009 |
| WO | 2010085774 A1 | 7/2010 |
| WO | 2010091111 A1 | 8/2010 |
| WO | WO 2010128091 A1 * | 11/2010 |

OTHER PUBLICATIONS

Phillips et al., Prenatal Diagnosis of Sickle Cell Anemia by Restriction Endonuclease Analysis: HindIII Polymorphisms in Gamma-Globin Genes Extend Test Applicability; Proc. Natl. Acad. Sci. USA, 1980, 77(5), 2853-2856.*
Soundararajan et al., DNA Binding and Recognition by the IIs Restriction Endonuclease MboII, J. Biological Chem., 2002, 277(2), 887-895.*
Broad Institute, Broad/Illumina Genome Analyzer Boot Camp, 2012, 1 (reference for date of initial slide publication/presentation).*
Broad Institute, Broad Instittue/Illumina GA Boot Camp: Sample Preparation, Module 1: Overview, Slides, Feb. 2010, 1-76.*
Morgan et al., Rational Engineering of Type II Restriction Endonuclease DNA Binding and Cleavage Specificity, Nucleic Acids Research, 2009, 37(15), 5222-5233.*
Soundararajan et al., DNA Binding and Recognition by the IIs Restriction Endonuclease MboII, Journal of Biological Chemisry, 2002, 887-895.*
Harismendy et al., Evaluation of Next Generation Sequencing Platforms for Population Targeted Sequencing Studies, Genome Biology, 2009, 1-13.*
Huang et al., Isolation of *C. elegans* Deletion Mutants Following ENU Mutagenesis and Thermostable Restriction Enzyme PCR Screening, Molecular Biotechnology, 2006, 32, 83-86.*
Young et al., A New Strategy for Genome Assmbly Using Short Sequence Reads and Reduced Representation Libraries, Genome Research, 2010, 20, 249-256.*
Baird N.A., Etter P.D., Atwood T.S., Currey M.C. et al. (2008) Rapid SNP Discovery and Genetic Mapping Using Sequenced RAD Markers. PLoS ONE 3(10): e3376.
Gore M.A., Chia J-M., Elshire R.J. et al. (2009) A First-Generation Haplotype Map of Maize. Science 326 (5956):1115-7.
Sanchez C.C., Smith T.P.L., Weidmann R.T. et al. (2009) Single nucleotide polymorphism discovery in rainbow trout by deep sequencing of a reduced representation library. BMC Genomics 10:559.
Wang J., Wang W., Li R. et al. (2008) The diploid genome sequence of an Asian individual. Nature 456(7218):60-5.
Li R., Li Y., Fang X. et al., (2009) SNP detection for massively parallel whole-genome resequencing. Genome Res. 19 (6):1124-32.
Sherry S.T., Ward M.-H., Kholodov M. et al. (2001) dbSNP: the NCBI database of genetic variation. Nucleic Acids Research 29(1):308-11.

(Continued)

*Primary Examiner* — Maria Leavitt
*Assistant Examiner* — Amy M Bunker
(74) *Attorney, Agent, or Firm* — Westman, Champlin & Koehler, P.A.; Z. Peter Sawicki; Amanda M. Prose

(57) ABSTRACT

A DNA library, and a preparing method thereof, a method of determining DNA sequence information, an apparatus and a kit for detecting SNPs, and a method for genotyping may be provided. The method for preparing the DNA library may comprise the steps of: digesting a genomic DNA sample using a restriction endonuclease to obtain a digested product, wherein the restriction endonuclease comprises at least one selected from the group consisting of Mbo II and Tsp 45I; separating the digested product to obtain DNA fragments having a length of 100 bp to 1,000 bp; end-repairing the DNA fragments to obtain an end-repaired DNA fragments; adding a base A to the end of the end-repaired DNA fragments to obtain DNA fragments having a terminal base A; and ligating the DNA fragments having the terminal base A with sequencing adaptors to obtain the DNA library.

4 Claims, 6 Drawing Sheets

(56) References Cited

OTHER PUBLICATIONS

Ding C., Jin S. (2009) High-Throughput Methods for SNP Genotyping. Methods Mol Bio 578:245-254.
International Search Report; PCT/CN2011/079971; Dec. 15, 2011.
Written Opinion of the International Searching Authority; PCT/CN2011/079971; Dec. 15, 2011.
Office Action issued for related Chinese Patent Application No. 201010555192.4, dated Nov. 2, 2012.
Office Action issued for related Chinese Patent Application No. 201010555192.4, dated Jul. 16, 2013.
Office Action issued for related Chinese Patent Application No. 201010555192.4, dated Jan. 13, 2014.
Search Opinion issued for related European Patent Application No. 11843141.0, dated Sep. 13, 2013.
Supplementary European Search Report issued for related European Patent Application No. 11843141.0, dated Sep. 13, 2013.
Wu, X. et al. "SNP discovery by high-throughput sequencing in soybean", BMC Genomics, Biomed Central Ltd., vol. 11, No. 1, p. 469, Aug. 11, 2012.
Sanchez C. C. et al., "Single nucleotide polymorphism discovery in rainbow trout by deep sequencing of a reduced representation library", BMC Genomics, Biomed Central Ltd., vol. 10, No. 1, p. 559, Nov. 25, 2009.
Altshuler D. et al., "An SNP map of the human genome generated by reduced representation shotgun sequencing", Nature: international weekly journal of science (and supplementary information), Nature Publishing Group, vol. 407, p. 513-516, Sep. 28, 2000.

* cited by examiner

A

B

C

D

DNA LIBRARY, PREPARATION METHOD THEREOF, AND DEVICE FOR DETECTING SNPS

CROSS-REFERENCE TO RELATED APPLICATION

This Application is a 371 National Stage Application of International patent application Serial No. PCT/CN2011/079971, filed Sep. 21, 2011, and published as WO 2012/068919, which claims priority to and benefits of Chinese Patent Application No. 201010555192.4, filed with the State Intellectual Property Office of the People's Republic of China (SIPO) on Nov. 23, 2010, the entire content of which are hereby incorporated by reference.

FIELD

The present disclosure relates to the field of molecular biology, in particular, the present disclosure provides a DNA library and a preparation method thereof, a method for identifying DNA sequence information, an apparatus and a kit for SNPs detection, as well as a method for genotyping.

BACKGROUND

Single nucleotide polymorphism (SNP) refers to a mutation of a single nucleotide nucleotide in genome, which has a great number and rich polymorphism. SNP is considered to be the most ideal genetic markers in the study of comparative genomics and evolutionary genomics, while SNP is also considered to be effective molecular markers in the study of disease-related genetics and pharmacological genomics. Regardless of which application field, it has to detect and genotype a large number of SNPs in samples. Although deep re-sequencing of genome is the most direct and effective way to detect SNPs, the cost of genome sequencing is more expensive which cannot meet the requirements of large-scale samples' sequencing. So, many high-throughput methods for SNPs genotyping and commercial platform have been vigorously developed. (Chunming Ding and Shengnan Jin. (2009). High-throughput methods for SNP genotyping. Single Nucleotide Polymorphisms, Methods in Molecular Biology. AA. Komar (eds), Humana Press. p 578, which is incorporated here by reference.)

However, the current method of detecting SNPs in samples still needs to be improved.

SUMMARY

The present disclosure is completed based on the following findings of the inventors:

Nowadays, commonly-used high-throughput platform for SNPs genotyping is mainly based on Illumina® BeadArray platform of single base extension technology and Affymetrix SNP microarray of differential hybridization method, both of which are based on existing SNPs information, by the method of designing synthetic probe and according to respective different principles to detect specific tag SNPs. At the same time it can design different SNPs combinations to be tested direct to different traits of association analysis which make the design of detection more flexible and higher specific. However, these methods have some limitations, such as the probe need to go through a rigorous screening design and not all tag SNPs can meet these design requirements. At the same time, the requirement of Chip synthesis is high-demanding, general laboratory is hard to achieve, and purchasing commercial chip leads to high-costs and requires specialized scanning equipment and analysis software. In addition, an important limitation factor is the probe design in this method must be established on the basis of known SNPs database which cannot find out unknown SNPs (Chunming Ding and Shengnan Jin. (2009). High-Throughput Methods for SNP Genotyping. Single Nucleotide Polymorphisms, Methods in Molecular Biology. AA. Komar (eds), Humana Press. p 578, which is incorporated here by reference.)

Further, a combination of restriction endonucleases and next-generation sequencing techniques (NGS), several existing methods used for polymorphism detection of specific point in genome-wide [Nathan A, Baird, Paul D, et al. (2008). Rapid SNP Discovery and Genetic Mapping Using Sequenced RAD Markers. PLoS ONE, 3(10):3376.; Michael A. Gore, et a/42009). A First-Generation Haplotype Map of Maize. Science, 326:1115, which is incorporated here by reference], or a sequencing of DNA tags depending on association of restriction cleavage locis (RAD) (Nathan A, Baird, Paul D, et al. (2008) Rapid SNP Discovery and Genetic Mapping Using Sequenced RAD Markers. PLoS ONE, 3(10):3376; Sanchez C C, Smith T P L, Wiedmann R T, et al. (2009). Single nucleotide polymorphism discovery in rainbow trout by deep sequencing of a reduced representation library. BMC Genomics, 10:559, which is incorporated here by reference), or at least using one rare locus restriction endonuclease, and processes of enzyme cleavage and building database are complicated, while some of these methods are easier to introduce and amplify the deviation of the sequence because of PCR amplification process.

The present disclosure directs to solve at least one of the problems existing in the art to at least some extent. Therefore, one aspect of the present disclosure provides a method for preparing a DNA library which can prepare the DNA library for SNPs detection. According to an embodiment of the present disclosure, the method for preparing the DNA library comprises the steps of: digesting a genomic DNA sample using a restriction endonuclease to obtain a digested product, wherein the restriction endonuclease comprises at least one selected from the group consisting of Mbo II and Tsp 45I; separating a DNA fragment having a length of 100 bp-1,000 bp from the digested product; end-repairing the DNA fragment to obtain an end-repaired DNA fragment; adding a base A at the end of the end-repaired DNA fragment to obtain a DNA fragment having a terminal base A; and ligating the DNA fragment having the terminal base A with a sequencing adaptor to obtain the DNA library. With the method of preparing the DNA library according to the embodiment of the present disclosure, it is possible to efficiently construct the DNA library of a sample, so that by sequencing the DNA library it can obtain a DNA sequence information of the sample, eventually by SNPs data analyzing of DNA sequence information it can obtain SNPs information of a sample DNA. Moreover, the inventor has found out that the above method has simple process, is easy to operate, is easy to standardize operational processes and has lower cost. In addition, the inventors have also surprisingly found that based on the above method for the same samples, when using a candidate of different restriction endonucleases to construct the DNA library, the stability and the repeatability of sequencing data obtained are very good.

Further, the present disclosure also provides a DNA library which is obtained obtained according to the method for preparing the DNA library of an embodiment of the present disclosure.

According to another aspect of the present disclosure, the present disclosure also provides a method of determining a DNA sequence information. According to an embodiment of the present disclosure, the method of determining the DNA sequence information comprises the steps of constructing a DNA library according to the method for preparing the DNA library of an embodiment of the present disclosure; and sequencing the DNA library to obtain the DNA sequence information. Based on this method, it is possible to effectively obtain the DNA sequence information in the DNA library; thereby it is possible to subject the DNA sequence information to SNPs data analysis to obtain SNPs information. Further, inventor has surprisingly found out that by using the method according to the embodiment of the present disclosure to determine the DNA sequence information, it is possible to efficiently reduce the deviation problem of the data and reduce the cost.

According to another aspect of the present disclosure, the present disclosure also provides an apparatus for detecting SNPs. According to an embodiment of the present disclosure, the apparatus for detecting SNPs comprises: a DNA-library-preparing unit, used to prepare a DNA library; a sequencing unit, connected to the DNA-library-preparing unit and used to sequence the DNA library and obtain a DNA sequence information; and a SNP s-data-analysis unit, connected to the sequencing unit, and used to subjecting the DNA sequence information to SNPs data analysis to obtain accurate SNPs information, and it can be applied to large-scale number of samples' SNPs detection.

According to another aspect of the present disclosure, the present disclosure also provides a kit for detecting SNPs. According to an embodiment of the present disclosure, the kit for detecting SNPs comprises: a restriction endonuclease, comprising at least one selected from the group consisting of Mbo II and Tsp 45I. Thus, using the kit, can easily detect the samples SNPs.

According to another aspect of the present disclosure, the present disclosure also disclosure also provides a method for genotyping. According to an embodiment of the present disclosure, the method for genotyping comprises providing a genomic DNA sample; preparing a DNA library of the genomic DNA sample according to the method for preparing the DNA library of the embodiment of the present disclosure; sequencing the DNA library to obtain a DNA sequence information; subjecting the DNA sequence information to SNPs data analysis to obtain SNPs information of the sample; and genotyping the sample based on the SNPs information. By using above method of constructing sample DNA library meeting the requirement for SNPs detection and sequencing the DNA library to obtain a DNA sequence information, then subjecting the DNA sequence information to SNPs data analysis, it is able to efficiently obtain SNPs information of the sample DNA, thereby based on obtained SNPs information of the sample combining with species existing genotype information, it is able to efficiently genotype the sample. In addition, inventor has found out that the genotyping method has a simple process and is easy to operate, and the cost is very low.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference the accompanying drawings, in which.

DETAILED DESCRIPTION

Figure 1:
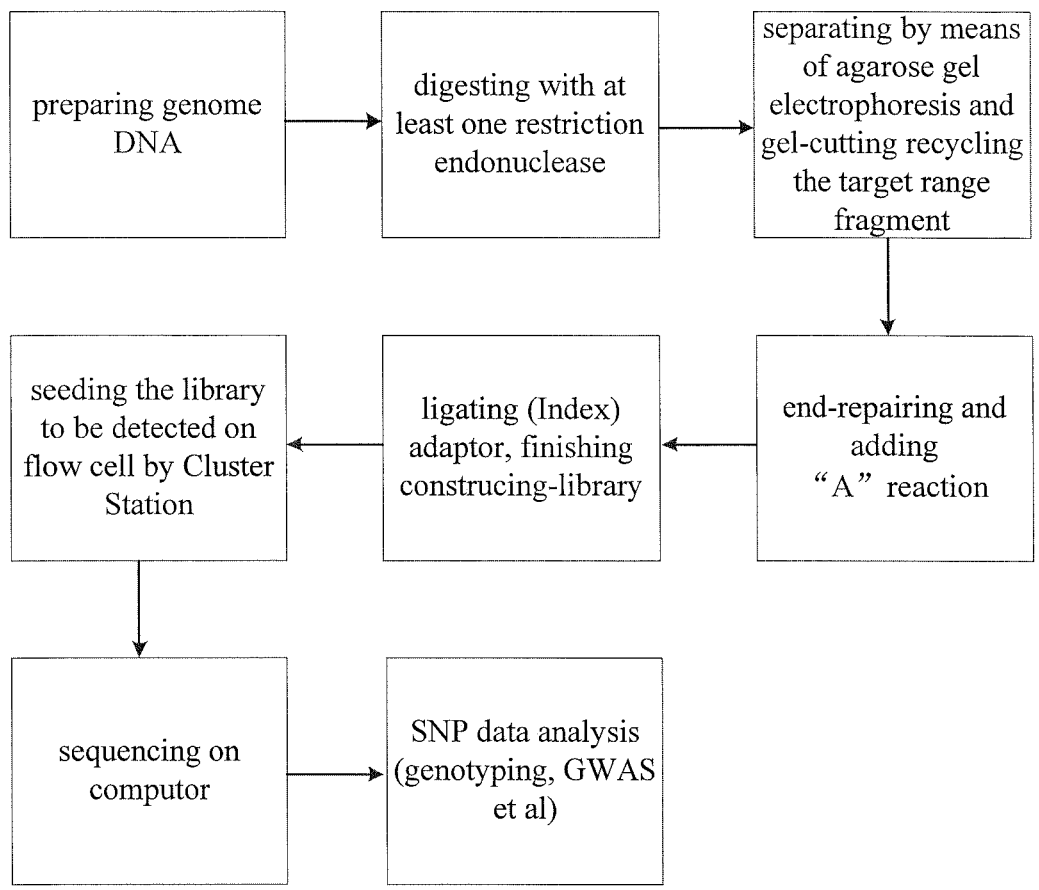
FIG. 1 is a flow chart of SNPs detection method according to an embodiment of the present disclosure.

Reference will be made in detail to embodiments of the present disclosure. Examples of the embodiments will be demonstrated in figures. The same or similar elements and the elements having same or similar functions are denoted by like reference numerals throughout the descriptions. The embodiments described herein with reference to drawings are explanatory, illustrative, and used to generally understand the present disclosure. The embodiments shall not be construed to limit the present disclosure.

It is noted that terms such as "first" and "second" are used herein for purposes of description and are not intended to indicate or imply relative importance or implicitly specified the number of the technical features indicated. Thus the features defined with "first", "second" may be explicitly or implicitly include one or more feathers thereof. Further, in the description of the present disclosure, "more" refers to two or more than two unless expressly described otherwise.

DNA Library, and Method of Constructing and Sequencing Thereof

According to one aspect of the present disclosure, the present disclosure provides provides a method for preparing a DNA library which can prepare the DNA library for detecting SNPs. Specifically, according to an embodiment of the present disclosure, referring to FIG. 1, the method comprises the steps of:

First of all, a genomic DNA sample is digested by using a restriction endonuclease to obtain a digested product, wherein the restriction endonuclease comprises at least one selected from the group consisting of Mbo II and Tsp 45I. According to an embodiment of the present disclosure, the restriction endonuclease further comprises one selected from the group of Hind III and Bcc I. According to an embodiment of the present disclosure, a source of the DNA sample is not subjected to special restrictions. According to a specific example of the present disclosure, the genomic DNA sample may be derived from currently existing whole-genome sequence data of any species, specifically, the genomic DNA sample may be obtained from a individual, a single cell or a tissue of the species. Preferably, according to an embodiment of the present disclosure, the genomic DNA sample is human genomic DNA. In addition, according to an embodiment of the present disclosure, the extraction method of the genomic DNA is not subjected to special restrictions. Skilled in the art may be appreciated that different extraction methods of genomic DNA can be selected according to the different species and samples, specifically, it may be done in accordance with a method known to those skilled in the art (including using a commercial kit), such as plant tissue or microorganisms may be extracted by standardized CTAB method, human blood genomic DNA may be completed by using QIAamp® DNA Mini Kit (QIAGEN) et al. According to the method for constructing the DNA library of an embodiment of the present disclosure, the obtained genomic DNA need to kept intact as much as possible, eg. need to reduce excessive small DNA fragments produced by artificial fracture, generally, a standard reaching more than 23K detected by agarose gel electrophoresis is regarded as qualified, at the same time DNA purity is need to be high as much as possible to avoid affecting the digestion.

In addition, the inventor of the present disclosure has found out that constructing constructing the DNA library must choose at least one restriction endonuclease to digest the genomic DNA, the employed restriction endonuclease is slightly different depending on the different species, commonly-used recognition sequence is 5 or 6 bases of type II restriction endonucleases, further II s-type restriction endonuclease whose cleavage loci is beyond the recognition loci may also be used. In general, the employed restriction endonuclease should be one or two, because using excessive restriction endonuclease is difficult to complete digestion in one-tube reaction system, it may not only increase the complexity of the operation, but also lead to incomplete digestion or appearance of star activity. While nowadays, there are many commercial restriction endonuclease to be chosen, such as NEB (NEW ENGLANG BioLabs) company, TaKaRacompany et al. Therefore, the inventor of the present application have conducted a great deal of screening work, and chosen a preferable restriction endonuclease according to an embodiment of the present disclosure, the restriction endonuclease is at least one group selected from followings: (1) Mbo II; (2) Tsp 45I; (3) Mbo II and Hind III; and (4) Mbo II and Bcc I.

Secondly, the digested product is separated to obtain a DNA fragment having a length of 100 bp-1,000 bp. According to an embodiment of the present disclosure, a separating and a recycling method of the digested product are not subjected to special restrictions, it may be conducted in accordance with a method known to those skilled in the art.

According to an embodiment of the present disclosure, the digested product is isolated by using 2% agarose gel electrophoresis, and then the gel is cut targeting a length having the range of 100 bp-1,000 bp, and then the DNA fragment within the targeting range may be recycled by using commercial gel-recycling kit (such as MinElute® PCR Purification Kit (QIAGEN)). According to an embodiment of the present disclosure, DAN fragment has a 100 bp-1,000 bp, further, the DNA fragment has a length of 200 bp-700 bp.

Next, the DNA fragment is subjected to end-repairing step to obtain an end-repaired DNA fragment, and a base A is added at the end of the end-repaired DNA fragment to obtain a DNA fragment having a terminal base A. According to an embodiment of the present disclosure, reactions of end-repairing the DNA fragments and adding the "A" use standardized process, specific process thereof is as followings: adding the above DNA fragment, 10 mM dNTP, T4 DNA polymerase, Klenow fragment, T4 polynucleotide kinase and T4 DNA ligase buffer (with 10 mM ATP) to a reaction system, incubating at 20° C. for 30 minutes, then recycling the DNA fragments, and then adding the end-repaired DNA fragment, dATP, Klenow fragment, Klenow (3'-5'exo-) to another reaction system, then reacting at 37° C. for 30 minutes.

Finally, the DNA fragment having the terminal base A is ligated with a sequencing sequencing adaptor to obtain the DNA library. According to an embodiment of the present disclosure, the selection of the sequencing adaptor is not subjected to special restrictions; it may choose different connectors depending on different sequencing technology methods (high throughput sequencing platform). According to an embodiment of the present disclosure, a method based on synthesis-sequencing principle from Illumina® is employed, so the sequencing adaptor is selected with corresponding Illumina® adaptor, thus a library fragment can be ligated with a flow cell, so that a following sequence process can be continued. According to an embodiment of the present disclosure, the sequencing adaptor does not need to include a binding loci of amplification primer (because the method for constructing the DNA library according to an embodiment of the present disclosure does not involve PCR amplification), however, it needs a binding loci of a sequencing primer, further, in order to separate the DNA libraries preparing from different samples after sequencing, 8 by tag sequence and tag sequencing primer sequence may also be brought into one adaptor which may conveniently sequence the different libraries directly after being mixed using computer, so that it can be applied to the library-constructing and the sequencing of large scale samples. In addition, according to an embodiment of the present disclosure, after finishing the library construction, Agilent® Bioanalyzer 2100 can be used to detect the library fragments distribution, and Q-PCR can be used to quantify the libraries.

By using the method for constructing the DNA library of an embodiment of the of the present disclosure, it can efficiently construct the sample DNA library, by sequencing the DNA library to obtain a sequence information of the sample DNA and subjecting the sequence information of the sample DNA to SNPs data analysis, it can accurately obtain SNPs information of the sample DNA, thereby the sample SNPs information can be subjected to many relative science study. Further, the inventor has found out that the above method has a simple process, the operation procedure can be standardized, then the operation is convenient, and the cost is low. In addition, the inventor has also surprisingly found out that for the same sample, based on the above method, using a candidate of different restriction endonucleases to construct the DNA library, the stability and the repeatability of the sequencing data obtained are very good; while multiple and parallel library construction for the same sample, the sequencing data is stable which indicates that the parallelism and the repeatability of the method for constructing the DNA library according to an embodiment of the present disclosure are good.

Further, according to an embodiment of the present disclosure, the present disclosure provides a method for constructing a DNA library which comprises:
1) digesting a genomic DNA sample using at least one restriction endonuclease to obtain a digested product;
2) separating a DNA fragment having a length of 100 bp-1,000 bp from the digested product;
3) end-repairing the DNA fragment obtained from step 2);
preferably, also comprise following steps:
4) adding a base A at the end of the DNA fragment obtained from step 3);
preferably, also comprise following steps:
5) ligating the DNA fragment obtained from step 4) with a sequencing adaptor.

According to some specific examples of the present disclosure, the step 1) of the above method for constructing a DNA tag library according to an embodiment of the present disclosure: all sample genomic DNA may be derived from any species which already have whole genomic sequence data nowadays, the genomic DNA may be derived from a individual, a single cell or a tissue of the species. Preferably, the genomic DNA sample is human genomic DNA. To the skilled in the art, the extraction method of the genomic DNA, based on different species and samples, may be completed in accordance with a method known to those skilled in the art (including using a commercial kit), such as plant tissue or microorganisms may be extracted by standardized CTAB method, human blood genomic DNA may be completed by using QIAamp® DNA Mini Kit (QIAGEN) et al. The obtained genomic DNA should keep intact as much as possible, and reduce excessive small DNA fragments produced by artificial fracture, generally, a standard reaching more than 23K detected by agarose gel electrophoresis is regarded as qualified, at the same time DNA purity should be ashigh as possible to avoid affecting the digestion. In addition, the genomic DNA sample is subjected to digestion by selecting at least one restriction endonuclease which is slightly different depending on the studied species, commonly-used recognition sequence is 5 or 6 bases of type II restriction endonucleases, further II s-type restriction endonuclease whose cleavage loci is beyond the recognition loci may also be used. In general, the employed restriction endonuclease should be one or two, because using excessive restriction endonuclease is difficult to complete digestion in one-tube reaction system, it may not only increase the complexity of the operation, but also lead to incomplete digestion or appearance of star activity. Nowadays, there are many commercial restriction endonuclease to be chosen, such as NEB (NEW ENGLAND BioLabs) company, TaKaRa company et al., the reaction condition is based on a instruction provided by the restriction endonuclease to guarantee to achieve a preferable digested effect. Preferably, the digestion is a fully-completed digestion. According to an embodiment of the present disclosure, making the human genome as the main study object, different digestion combinations have been designed, especially a digestion combination shown in FIG. 1 is preferred. Wherein, names of the restriction endonucleases are based on the announcement of NEB Company.

According to some specific examples of the present disclosure, the step 2) of the method for constructing the DNA tag library according to an embodiment of the present disclosure: the digested genomic fragments are recycled according to the method known by skilled in the art, such as using an agarose gel electrophoresis with an appropriate concentration to digest the DNA fragments. Generally, for recycling DNA fragments within a range of below 1 kb, 2% agarose gel is an appropriate choice. Further, the restriction endonuclease may cut the human genome into a substantial same length distribution (such as 100 bp-10.00 bp), the fragments of this range distribution is to obtain a part of genome, and too much differences of fragment length in a library may affect the quality of the final sequencing data, and may lead to a large increase in cost. According to an embodiment of the present disclosure, the lengths of the DNA fragments obtained are 100 bp-1,000 bp, further, according to an embodiment of the present disclosure, the lengths of the DNA fragments are 200 bp-700 bp. To effectively obtain the DNA fragments having this length range, the inventor of the present disclosure have made a lot of study and tireless efforts and have found out that the restriction endonuclease in the step 1) of the present method is preferably at least one group selected from followings (1)-(4) according to an embodiment of the present disclosure (shown in Table 1): (1) Mbo II; (2) Tsp 45I; (3) Mbo II and Hind III; and (4) Mbo II and Bcc I.

According to some specific examples of the present disclosure, the steps 3) and 4) of the method for constructing DNA tag library according to an embodiment of the present disclosure: reactions of end-repairing and adding a base "A" is performed by using standardized process after recycling the digested DNA fragments, specific steps are as followings: adding the recycling DNA, 10 mM dNTP, T4 DNA polymerase, Klenow fragment, T4 polynucleotide kinase and T4 DNA ligase buffer (with 10 mM ATP) to a reaction system, incubating at 20° C. for 30 minutes, recycling the fragments, adding the end-repaired DNA fragment, dATP, Klenow fragment, Klenow (3'-5'exo-) to another reaction system, then reacting at 37° C. for 30 minutes.

According to some specific samples of the present disclosure, the above step 5) of the method for constructing DNA tag library according to an embodiment of the present disclosure, an adaptor is ligated with the restriction fragment, the choice of the adaptor is different depending on different sequencing technology methods (high throughput sequencing platform). The method based on synthesis-sequencing principle from Illumina® employed in the embodiment of the present disclosure, thus, Illumina® adapter sequence includes complementary sequence of oligo nucleotide connected with flow cell for sequencing to facilitate library fragments connected to the flow cell. Since the prevent disclosure does not use the method of PCR amplification, thus, the adding adaptor does not need to include the binding loci of amplification primer, however it needs the binding loci of the sequencing primer, in order to separate the DNA libraries preparing from different samples after sequencing, 8 bp tag Index tag sequence and index tag sequencing primer sequence may also be brought into one adaptor which may conveniently sequence the different libraries directly after being mixed using computer. After finishing the library construction, the library fragments distribution is detected by Agilent® Bioanalyzer 2100, the libraries are quantified by Q-PCR.

By using the method for constructing the DNA library according to an embodiment of the present disclosure, it can efficiently construct the sample DNA library, after sequencing the DNA library; it can accurately obtain the sequence information of the sample DNA, by subjecting the sample DNA sequence information to SNPs data analysis, it can be successfully applied to many downstream relative science study. Further, the inventor has found out that the above method has a simple process, the operation procedure can be standardized, then the operation is convenient, and the cost is low. In addition, the inventor has also surprisingly found out that for the same sample, based on the above method, using different restriction endonucleases to construct the DNA library, the sequence data is stable, the repeatability is good; while multiple and parallel library construction for the same sample, the sequencing data is stable which indicates that the parallelism and the repeatability of the method for constructing the DNA library according to an embodiment of the present disclosure are good.

According to another aspect of the present disclosure, the present disclosure also provides a DNA library which is constructed according to the method for constructing the DNA library of the present disclosure. The DNA library can be efficiently applied to high-throughput sequencing technology such as Solexa technology, thereby by obtaining a sample DNA sequence information, the sample DNA sequence information can be subjected to SNPs data analysis, so as to obtain SNPs information of the sample DNA to prepare for applying to downstream relative science study.

According to another aspect of the present disclosure, the present disclosure also provide a method of determining a DNA sequence information, which is accomplished by sequencing the DNA library constructed according to the method for constructing the DNA library of an embodiment of the present disclosure. According to specific examples of the present disclosure, the method of determining a DNA sequence information comprises the steps of: constructing the DNA library of sample genome DNA according to the method for preparing the DNA library of an embodiment of the present disclosure; and sequencing the DNA library to obtain the DNA sequence information. Further, according to an embodiment of the present disclosure, the method of determining a DNA sequence information also comprises a step of subjecting the DNA sequence information to SNPs data analysis to obtain SNPs information. According to an embodiment of the present disclosure, the DNA library is sequenced by using one of the groups selected from GS sequencing platform, GA sequencing platform, HiSeg2000™ sequencing platform and SOLiD™ sequencing platform. Based on the method, the sequence information of sample DNA in DNA library can be efficiently obtained, thereby the DNA sequence information can be subjected to SNPs data analysis to obtain sample DNA SNPs information, and then according to obtained sample SNPs information, various samples are subjected to science study such as genotyping. Further, the inventor has surprisingly found out that by determining sample DNA sequence information according to an embodiment of the present disclosure, it can effectively reduce the deviation problem produced from data, and the operability and the parallelism of this method are good, the process can also be effectively simplified when sequencing large scale samples, and the cost of sequencing is also reduced.

Apparatus, Kit and Genotyping Method for Detecting SNPs

Figure 10:
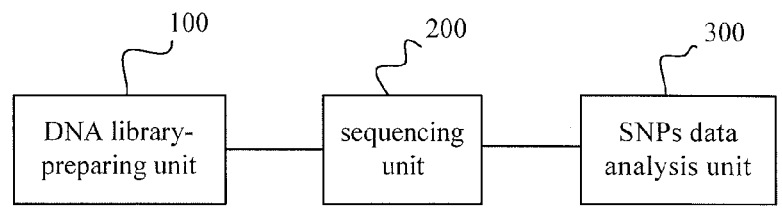
FIG. 10 is a schematic diagram of an apparatus for detecting SNPs according to an embodiment of the present disclosure.

According to another aspect of the present disclosure, the present disclosure also provides an apparatus for detecting SNPs. Referring to FIG. 10, according to an embodiment of the present disclosure, the apparatus 1000 for detecting SNPs comprises: a DNA library-preparing unit 100, a sequencing unit 200 and a SNPs-data-analysis unit 300.

According to an embodiment of the present disclosure, the DNA library-preparing unit 100 is used to prepare a DNA library, such as adopting any apparatus suitable for the above library-constructing method as the DNA library-preparing unit 100. The sequencing unit 200, connected to the DNA-library-preparing unit 100, can receive the DNA library prepared from the DNA-library-preparing unit 100, and subjected the received DNA library to sequencing to obtain a DNA sequence information. The SNPs-data-analysis unit 300, connected to the sequencing unit 200, can receive sample DNA sequence information obtained from the sequencing unit 200, and further subject the DNA sequence information to SNPs data analysis to obtain SNPs information. Skilled in the art can appreciate that any known apparatus in the art suitable for the above operation may be adopted as a component part of the above respective units. Further, the used term "connect" should be understood broadly, it may be connected directly, or may be connected indirectly through a intermediary, the specific implication of the above term may be understood in accordance with specific conditions for ordinary skilled in the art.

By using the above apparatus according to an embodiment of the present disclosure, it is convenient to subject the sample to SNPs detection, and can obtain accurate SNPs information. Further, the inventor of the present disclosure has found out that the apparatus for detecting the SNPs according to an embodiment of the present disclosure can be applied to large scale number of sample SNPs detection, so as to simplify the sequencing process, save the sequencing time and cost, and the obtained SNPs information is much more and accurate, the accomplishment of this use only need to add Index tag to DNA library in the DNA-preparing unit and subject the DNA library derived from various sample to mix-sequencing.

According to another aspect of the present disclosure, the present disclosure also provides a kit for detecting SNPs, according to an embodiment of the present disclosure, the kit comprises: a restriction endonuclease comprising at least one selected from the group consisting of Mbo II and Tsp 45I. Thus, by using this kit, sample SNPs can be conveniently detected.

According to another aspect of the present disclosure, the present disclosure also provides a method for genotyping, according to an embodiment of the present disclosure, the method for genotyping comprises: firstly, providing a genomic DNA sample; secondly, preparing a DNA library of the genomic DNA sample according to the method for constructing the DNA library of an embodiment of the present disclosure, sequencing the DNA library to obtain a DNA sequence information; subjecting the DNA sequence information to SNPs data analysis to obtain SNPs information of the sample; and genotyping the sample based on the SNPs information. Using the above method, by constructing high-quality sample DNA library in accordance with SNPs detection requirement, based on subjecting the high-quality DNA library to sequencing to obtain the sequence information of DNA sample, and then based on subjecting the DNA sequence information to SNPs data analysis to obtain accurate and effective SNPs information, and combining existing genomic information, the sample can be effectively subjected to genotyping. Further, the inventor of the present disclosure has found out that the method for genotyping has a simple process, the operation is easy, and the method for genotyping can be applied to large scale sample and the cost is very low.

It should be noted that, the method of determine the DNA sequence information according to the embodiments of the present disclosure is completed through tough creative labor and optimization by the inventor of the present disclosure.

Reference will be made in detail to embodiments of the present disclosure. It would be appreciated by those skilled in the art that the following embodiments are explanatory, and cannot be construed to limit the scope of the present disclosure. Embodiments do not indicate the specific technology or conditions, will be performed in in accordance with the techniques or conditions described the literature in the art (for example, referring to J. Sambrook, et al., <Molecular Cloning Laboratory Manual> translated by Huang P T, third version, science Press) or in accordance with the product instructions. Reagents or instruments do not label manufacturer, are both common products can be purchased commercially, such as purchased from Illumina company.

Embodiment does not indicate the specific technologies or conditions, the techniques described in accordance with the literature of the art or the conditions (for example, refer to J. Sambrook, waiting, Huang P T translated "Molecular Cloning Laboratory Manual, Third Edition, science Press) or in accordance with the product instructions. Reagent or instrument manufacturer does not indicate, both by the City purchase conventional products, for example, can be purchased from Illumina.

Embodiment 1

Determination of Preferable Restriction Endonuclease or Enzyme Combination

In accordance with the recognition sequence of the enzyme or the enzyme composition shown in the following Table 1, with known digestion recognition loci information, hg18 genomic sequence was taken as reference sequence, the genome was classified by length range with digestion loci as boundaries, finally the fragments having a range of 200 bp-700 bp were selected as libraries assemble to be tested. For skilled in the art, hg18 genomic sequence data can be downloaded from known database.

The data was filtered to generate in accordance with Illumina® HiSeg2000™ PE91 index sequencing parameter. As PE91 cycling number sequencing was employed in practice, so 91 bp base in both ends of each fragment in the above libraries assemble was taken as target area, the fragment within the selected range which included 91 bp in both ends of digestion loci in accordance with PE91 length sequencing reference was taken as target area, the SNP loci number in dbSNP v128 database being covered with target area, and the proportion of the above number in the total number of dbSNP v128 was counted.

As the reference sequence used is international public, in particular it does not involve the interference of other factors produced in the actual experiment (such as inevitable DNA fracture, incompletely digestion, et al.), thus the result obtained is the result under the ideal state, and also is the most optimal result.

TABLE 1 preferable enzyme composite of digested constructing-library of human genomic restriction endonuclease

| range of recycling fragment | enzyme or enzyme composite | detectable SNP number | coverage of dbSNP v128 |
|---|---|---|---|
| 200 bp-700 bp | Mbo II | 3338421 | 26.90% |
|  | Tsp 45I | 1579936 | 12.73% |

TABLE 1-continued preferable enzyme composite of digested constructing-library of human genomic restriction endonuclease

| range of recycling fragment | enzyme or enzyme composite | detectable SNP number | coverage of dbSNP v128 |
|---|---|---|---|
|  | Mbo II and Hind III | 3597897 | 28.99% |
|  | Mbo II and Bcc I | 4835970 | 38.97% |

Similar to the above detection method, the present inventor had also detected a large number of other enzymes or enzyme composite, the coverage of dbSNP v128 calculated was generally below 10%, the detection results of part of enzymes or enzyme composite are shown in Table 2:

TABLE 2 part of other enzymes and enzyme composite after detection

| range of recycling fragment | enzyme or enzyme composite | detectable SNP number | coverage of dbSNP v128 |
|---|---|---|---|
| 200 bp-700 bp | Bcc I | 751883 | 6.56% |
|  | Bgl II | 76415 | 0.67% |
|  | BamH I and BccI | 893795 | 7.80% |
|  | Hind III and BglII | 277079 | 2.42% |

As shown in Table 2, the detectable SNP number of enzymes or enzyme composite and the coverage of dbSNP v128 listed in Table 2 were both far lower than that listed in above Table 1.

Therefore, the enzymes or enzyme composite listed in Table 1 was the preferred solution.

Embodiment 2

Sequencing of Yanhuang 1# DNA Library

For human genome, such as specific technique method of the preferred enzyme composite listed in Table 1, four preferred digestion composite of the recycling fragment having a range of 200 bp-700 bp were selected to construct digestion constructing-library, data analysis and compare with the results listed in Table 1. The specific operations were as followings:

Human genomic DNA was extracted from blood cell of YanHuang 1# (YH 1), the extraction was accomplished by using QIAamp® DNA Mini Kit (QIAGEN). Finally, genomic DNA was dissolved in EB buffer, after quantification by assaying the absorbance value at A260 with NonoDrop ND-1000, 5 µg genomic DNA was subjected to digestion. All restriction endonucleases were purchased from NEB Company, the buffer was provided with enzyme, there are four enzyme composites.

The amount of the genomic DNA in each digesting reaction system was 5 µg, the amount of the restriction endonuclease was 20 U (unit defined by NEB), the most appropriate buffer and reaction condition were selected in accordance with different enzyme composite in each reaction, detailed shown in Table 3 below.

TABLE 3

| | Digesting system | | | |
|---|---|---|---|---|
| Enzyme composite | Mbo II | Tsp 45I | Mbo II + Hind III | Mbo II + Bcc I |
| Buffer | NEBuffer4 | NEBuffer1 + BSA | NEBuffer2 | NEBuffer1 + BSA |
| Reaction condition | 37° C., 1 hr | 65° C., 1 hr | 37° C., 1 hr | 37° C., 1 hr |

The above reaction buffers were all 10× stock solution, the reaction system was added up to 100 μL with Milli-Q water, the reaction was conducted in accordance with most appropriated condition.

Figure 2:
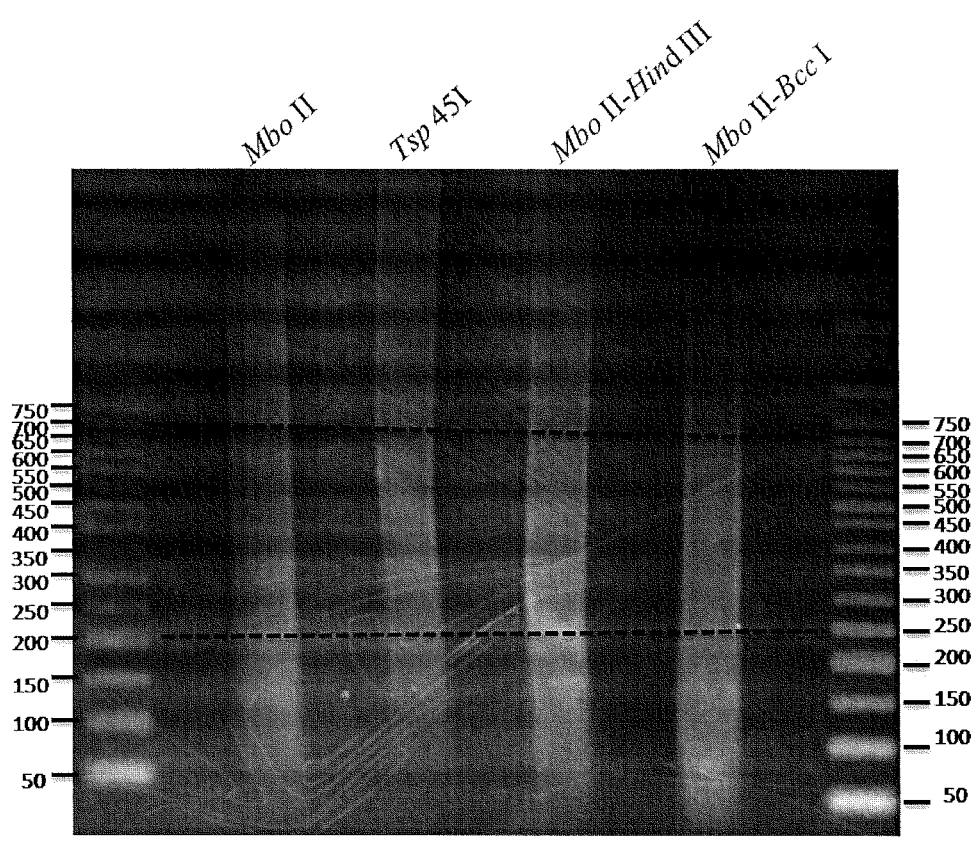
FIG. 2 is an electrophoresis test result of digested genomic DNA when constructing a DNA library according to the method for constructing a library of an embodiment of the present disclosure.

After separated the digested genomic DNA by 2% agarose gel electrophoresis (TAE buffer system) (FIG. 2), the hand-cut fragment having a length range of 200 bp-700 bp was gel-recycled by QIAquick® Gel Extraction Kit (QIAGEN), and then dissolved in 30 μL Milli-Q water.

| | |
|---|---|
| T4 DNA ligase buffer with 10 mM ATP | 10 μL |
| dNTPs | 4 μL |
| T4 DNA Polymerase | 5 μL |
| Klenow Fragment | 1 μL |
| T4 Polynucleotide Kinase | 5 μL |
| DNA | 30 μL |
| ddH$_2$O | up to 100 μL |

After reaction at 20° C. for 30 minutes, the end-repaired DNA fragment was recycled by using MinElute® PCR Purification Kit (QIAGEN). The sample was finally dissolved in 32 μL EB buffer.

The reaction of adding "A" was accomplished in accordance with following system:

| | |
|---|---|
| Klenow buffer | 5 μL |
| dATP | 10 μL |
| Klenow (3'-5' exo-) | 3 μL |
| DNA | 32 μL |

After incubation at 37° C. for 30 minutes, the product was purified by MinElute® PCR Purification Kit (QIAGEN) and dissolved in 35 μL EB buffer.

The reaction of ligating adaptor was as followings:

| | |
|---|---|
| 10x T4 DNA Ligation buffer | 5 μL |
| PCR-free Adapter oligo mix | 5 μL |
| T4 DNA Ligase | 5 μL |
| Sample DNA added with "A" | 35 μL |

Figure 3:
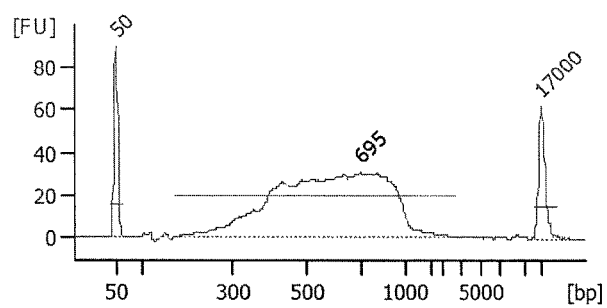
FIG. 3 is a Agilent® Bioanalyzer 2100 detection result of genomic DNA after combine-digested by four enzymes when constructing a DNA library according to the method for constructing a library of an embodiment of the present disclosure.
Figure 3:
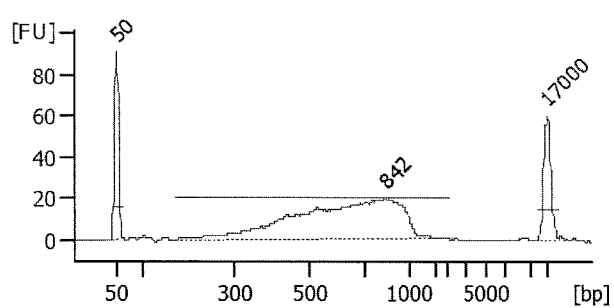
Figure 3:
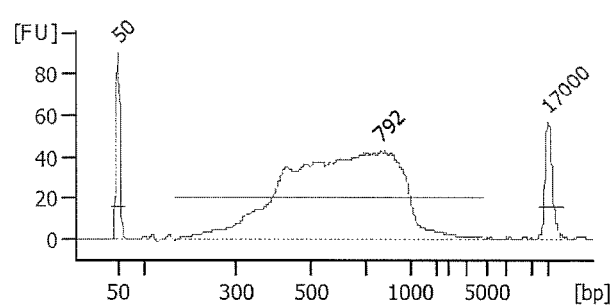
Figure 3:
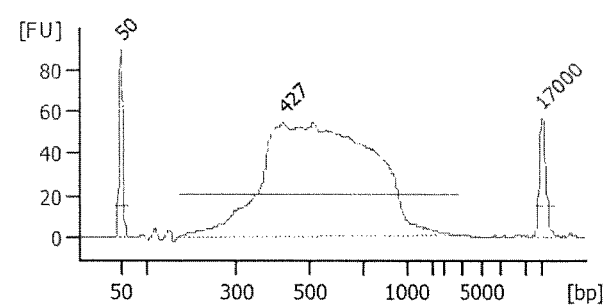

Ligation reaction was kept at 16° C. overnight. The adaptor was PCR-free index adaptor from Illumina® company, four libraries had unique 8 bp index sequence respectively, the constructed library was subjected to fragment distribution detection with Agilent® Bioanalyzer (FIG. 3, A-D). As seen from FIG. 3, the library-cut fragment range was 200 bp-700 bp, the fragment length increased about 120 bp after added with adaptor, as can be seen from FIG. 3, the fragment length of four libraries basically met the requirement, and the quality of the library met the sequencing requirement. The library constructed with Tsp 45I enzyme was named as YH library (YH library trial 1).

Four libraries were subjected to quantification by Q-PCR method and used as criteria, the three other libraries except Mbo II+Bcc I library was mixed with equal amount, while the amount of Mbo II+Bcc I library was twice amount of other libraries, a lane sequencing-amount of the flow cell of the hybrid library was subjected to computer sequencing. The sequencing was accomplished with Illumina® HiSeq2000™ sequencing system, the operation was fully in accordance with the corresponding operating instructions.

The data analysis was operated mainly in accordance with the method described in jun Wang et al., Nature (2008) (J Wang, et al., (2008). The diploid genome sequence of an Asian individual. Nature, 456:60), due to the bi-directional sequencing, so the row data was subjected to filter by setting paired sequencing reading direction and interval distance parameter (50 bp-2000 bp), the sequencing reading length which met the condition was matched in pairs, the sequencing reading length which did not meet the condition was matched individually, the matching method can use SOAP v2.20 to subject the sequencing reading length to matching to reference sequence hg18, the process of matching was allowed two base mismatching, calculating the proportion of all sequencing reading length could be matched to the reference sequence Finally, the proportion of these matching reading lengths which could fallen into the target area of different digestion composites (shown in Table 1) was detected, and the coverage and the cover depth of the target area were also detected, the results were shown in Table 4.

TABLE 4 results of data analysis

| | enzyme or composite for library construction | | | |
|---|---|---|---|---|
| | Mbo II | Tsp 45I | Mbo II-Hind III | Mbo II-Bcc I |
| sequencing total reading | 20406253 | 16964596 | 19182040 | 35838376 |

TABLE 4-continued results of data analysis

| | enzyme or composite for library construction | | | |
|---|---|---|---|---|
| | Mbo II | Tsp 45I | Mbo II-Hind III | Mbo II-Bcc I |
| data amount obtained (Mb) | 3673 | 3054 | 3453 | 6451 |
| base number matching to genome (proportion) | 2863709280 (78.0%) | 2137535730 (70.0%) | 2707424190 (78.4%) | 5241764970 (81.3%) |
| base number matching to the target area (proportion) | 1867134613 (65.2%) | 1232551200 (57.7%) | 1717052782 (63.4%) | 3873866058 (73.9%) |
| coverage of the target area | 81.10% | 89.00% | 72.60% | 87.70% |
| average cover depth of the target area | 3.13 | 4.67 | 2.675 | 4.643 |

As can be seen from the final results, the final results using the four digestion composites were basically same, except the Mbo II-Bcc I composite with double sample amount, other three sequencing libraries produced 3 Gb-4 Gb amount of data, and 70%-80% of these sequences could be matched to the genome, and among them there are 57%-73% of data could be matched to the target area, finally compared with the results shown in Table 1, 72%-90% of the target area was covered by sequencing, and the average cover depth was 3×-5×, thus, this method using the better digestion composite could obtain about 90% of the target area, and compared with the results shown in Table 1, the consistency of using different digestion composite was good.

Embodiment 3

SNPs Detection of Digestion Constructing-Library by Using Tsp 45I and Genotyping To detect the parallelism among different samples, and detection status of actual SNPs loci, except for using Yan-Huang 1# (labeled with YH) genome, present embodiment selected another genome from healthy male (labeled with DY) to subject to parallel experiment. According to the method similar to the embodiment 2, two DNA libraries were constructed by using TSP 45I enzyme respectively: YH library (YH library trail 2) and DY library.

SNP detection employed SOAPsnp program to filter according to the filter parameter of Q20. mean quality of best allele>20.copy number≤1.1, finally, SNPs numbers that actually obtained were calculated, and the proportion of this loci in dbSNP database. At the same time, according to YanHuang 1# whole genome known SNP loci information (Ruiqiang Li et al., (2010).SNP detection for massively parallel whole-genome sequencing. Genome Research, 19:1124), the SNP loci information within target area by Tsp 45I digestion constructing-library was selected and compared with the SNP loci identified in the present embodiment, the proportion of the SNPs loci actual detected in existing results were calculated.

Figure 4:
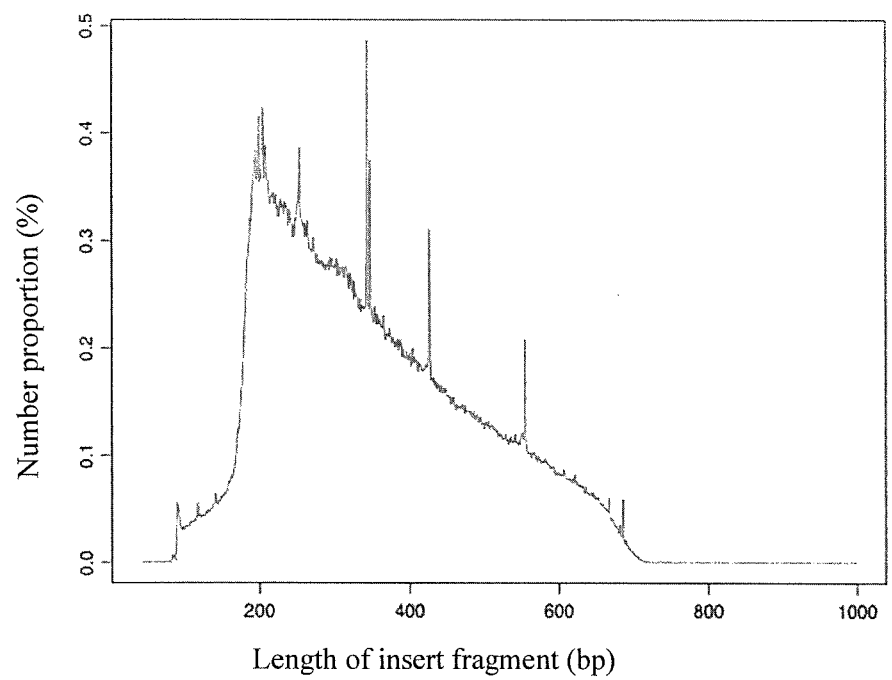
FIG. 4 is a statistical curve of inserted fragments range of a DY library constructed by using Tsp 45I according to the method for constructing the DNA library of an embodiment of the present disclosure.
Figure 5:
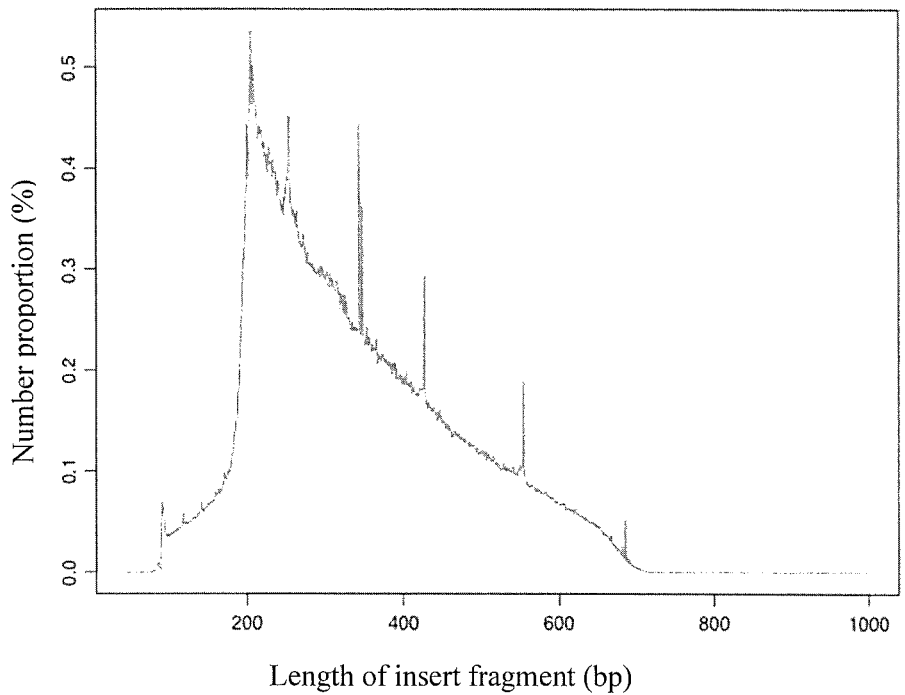
FIG. 5 is a statistical curve of inserted fragments range of a YH library constructed by using Tsp 45I according to the method for constructing the DNA library of an embodiment of the present disclosure.
Figure 6:
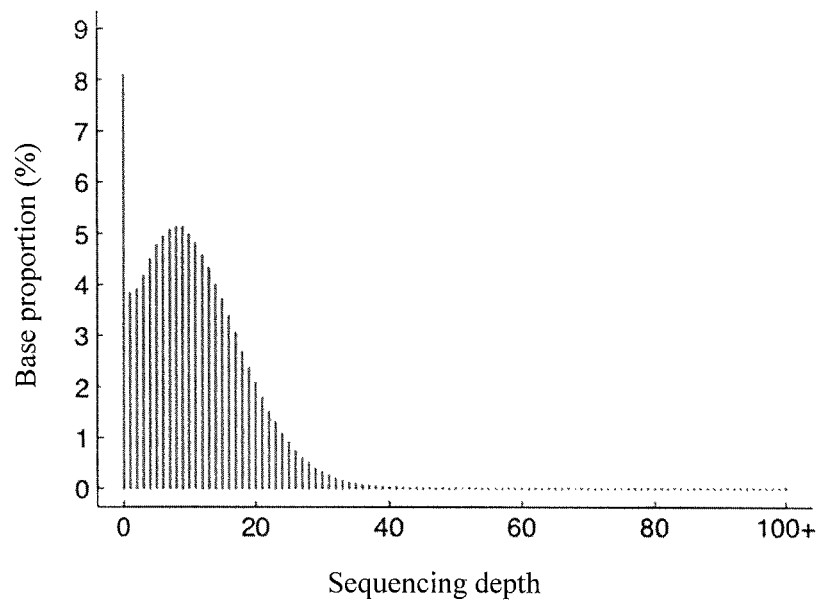
FIG. 6 is a statistical curve of sequencing depth of the DY library constructed by constructed by using Tsp 45I according to the method for constructing the DNA library of an embodiment of the present disclosure.
Figure 7:
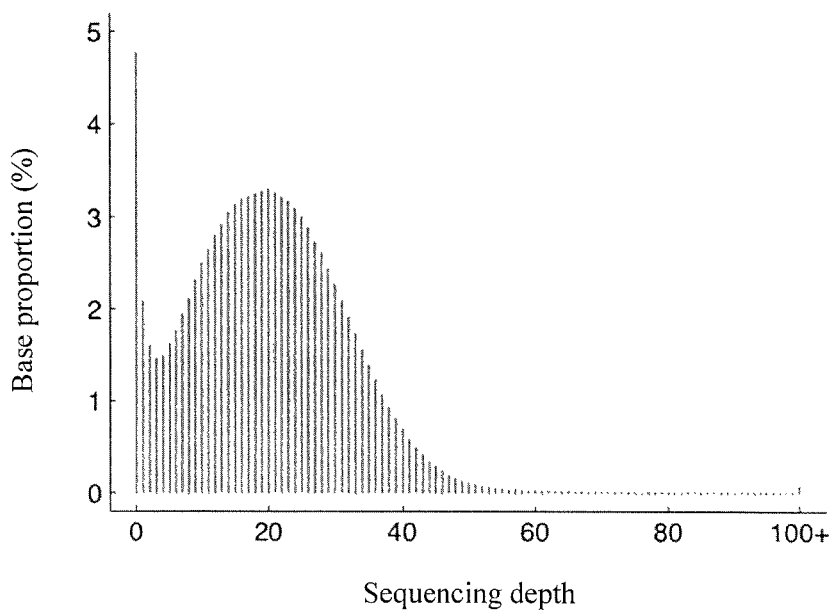
FIG. 7 is a statistical curve of sequencing depth of the YH library constructed by using Tsp 45I according to the method for constructing the DNA library of an embodiment of the present disclosure.

Specifically, the sequencing database of two libraries respectively constructed by using Tsp 45I was compared with reference of hg18 genome sequence, using these sequence that could be matched with reference genome correctly, the length distribution of insert fragment was calculated, the results showed that regardless using DY genome (FIG. 4) or YH genome (FIG. 5) to construct library, the insert fragments was normally distributed between 200 bp-700 bp, this was consistent with the initial experimental design and operation, and between the two libraries, the distribution ratio (Y coordinate) of sequencing data within the range of fragment length (X coordinate) was also consistent. Furthermore, the distribution of the sequencing data of the two libraries was calculated, wherein the average sequencing depth of the DY library (FIG. 6) was about 11×, the average sequencing depth of the YH library (FIG. 7) reached 20×, and the depth distribution of the two libraries was basically similar to Poisson distribution, while due to the final obtained sequencing data amount of the DY library was smaller than that of the YH library, so the sequencing depth thereof was lower.

Further statistical analysis of the results were shown in Table 5, wherein, 4.5 GB and 7.8 GB original data were obtained respectively after the sequencing of two libraries on computer, of which 76.8% and 84.6% could be matched to the hg18 reference genome, respectively, among this part data that could be matched correctly, 80.9% and 78.5% was located in the target area properly, respectively, and the proportion of statistical target area was covered by at least one of the sequencing data, two libraries were 91.9% and 95.2%, respectively. As can be seen from the data results, the method for constructing the library by using the restriction endonuclease could stably obtain more than 90% of the target area, and the ratio of the sequencing data was within the normal range.

TABLE 5 preliminary data analysis

| genome library | DY library | YH library |
|---|---|---|
| total sequencing data amount obtained (Mb) | 4540 | 7885 |
| data amount matching to reference genome Mb (proportion) | 3482 (76.84%) | 6664 (84.62%) |
| data amount matching to target area Mb (proportion) | 2818 (80.93%) | 5228 (78.47%) |

TABLE 5-continued preliminary data analysis

| genome library | DY library | YH library |
|---|---|---|
| target area at least being covered once Mb (proportion) | 242 (91.91%) | 251 (95.24%) |

Figure 8:
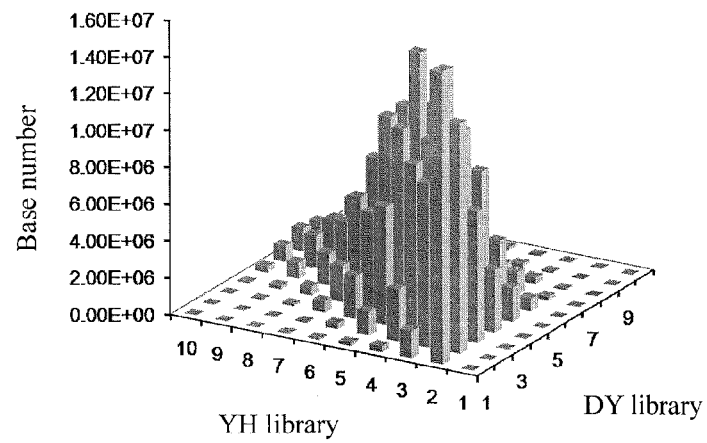
FIG. 8 is a comparison chart of the coverage depth consistency of target region between the DY library and the YH library constructed by using Tsp 45I respectively according to the method for constructing the DNA library of an embodiment of the present disclosure.
Figure 9:
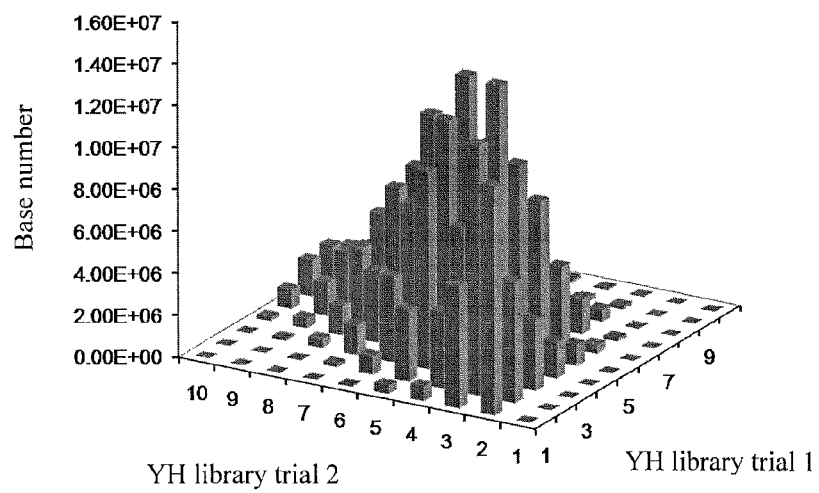
FIG. 9 is a comparison chart of the coverage depth consistency of target area between two constructed YH libraries according to the method for constructing the DNA library of an embodiment of the present disclosure.

To further compare the parallelism of the method for constructing library, the cover depth of different bases within target area was taken as a reference, three libraries constructed by using Tsp 45I were selected to perform two-two comparison, the parallelism between the YH library and the DY library (FIG. 8), the two constructed YH sample libraries (FIG. 9, "YH library trail 1" indicated the library constructed in embodiment 2, "YH library trail 2" indicated the library constructed in embodiment 3) was compared, wherein X and Y axes are corresponding to different samples or different experiment batches (labeled in FIG. 8 and FIG. 9), the coordinates were ascendingly divided into the corresponding intervals in accordance with the different cover depth, which indicated the ascending cover depth by 1-10. The Z-axis indicated the base numbers located at that depth interval, as can be seen from FIG. 8 and FIG. 9, regardless of different samples or different batches, the parallelism of constructing-library was good, the cover depths of most bases in the two libraries were basically the same.

At same time, analysis of the target area being co-covered between mutual-compared libraries indicated that, the consistency of the three libraries constructed in two times was good, wherein there were 3% of the target area having no sequencing data coverage in the two mutual-compared libraries, and the target area being covered was consistent with the 90%, further about 7% of the target area was covered in one library, which indicated that the parallelism of the method for constructing the library was 93% above.

As the YH library constructed in the second time, the average sequencing depth reached 20×, so this data was subjected to SNP detection, using SOAPsnp software, taken the Q20. mean quality of best allele>20.copy number≤1.1 as the filter parameter, taken h18 as the reference genome sequence, a total of 264K SNPs information had been received, by comparing with YH genome SNPs loci information published, there was 294K SNPs loci locating at target area of sequencing after Tsp 45I digestion, while there was 219K (74.6%) in SNPs loci obtained in this experiment was consistent, wherein 44K (17%) was false positive, 74K (25%) was false negative, determining through analysis, 28K (65%) loci of the false positive although being in reported YH genome were not detected, but it has been indexed in dbSNP database, which indicated that this could be filtered out in the YH reference SNP data integration for some reason, but it had been detected correctly in this experiment, so, by removing this part of reason, the false positive rate could be controlled within reasonable limits. While there was about 21K (28%) false negative portion because SNP was located within recognition loci of the restriction endonuclease, which led to the enzyme was not able to recognize and cleave, thus the target area fragment and SNP loci information had been lost, while another large part was caused by insufficient sequencing depth or low quality value of sequencing, this part was irrelevant with the present method, which could be further optimized by improving the sequencing amount in subsequent experiments.

To further validate the accuracy of the SNP loci obtained by this method, the data obtained was subjected to YH genome genotyping information comparison with the current mainstream genotyping chip (Illumina 1M BeadChip), there was 100K in about 1M of SNPs loci covered on the chip locating within the target area of the present method, however there was about 98K (90%) being covered by using the present method, in the co-covered portion, wherein the consistency of homozygous loci reached 99% above, and the consistency of heterozygous loci was 92%, the accuracy and the coverage were both good.

As can be seen from the above results, by the method for constructing the DNA library, determining the DNA sequence information and SNPs detection according to the embodiment of the present disclosure, pre-analog 90% above target area fragments were obtained effectively (Table 1), and the most SNPs information in this area had been detected successfully and accurately, these SNP information could be used for subsequent genotyping or SWAG study.

INDUSTRIAL APPLICABILITY

The DNA library and the preparing method thereof, the method of determining DNA sequence information, the apparatus and the kit for detecting SNPs and the genotyping method of the present disclosure can be applied to DNA sequencing, and further applied to SNPs detection and genotyping, and it can effectively improve the sequencing platform, such as the sequencing throughout of the Solexa sequencing platform.

Although the description of the embodiment of the present disclosure have been detailed described, it would be appreciated by those skilled in the art. According to all teachings already published, modifications and alternatives can be made with those details, these changes are all within the scope of the present disclosure. The whole scope of the present disclosure is provided by attached claims and any equivalents thereof.

Reference throughout this specification to "an embodiment," "some embodiments", "exemplary embodiment", "an example", "a specific example", or "some examples" means that a particular feature, structure, material, or characteristic described in connection with the embodiment or example is included in at least one embodiment or example of the present disclosure. Thus, the appearances of the schematic expressions of the phrases are not necessarily referring to the same embodiment or example of the present disclosure. Furthermore, the described particular features, structures, materials, or characteristics may be combined in any suitable manner in one or more embodiments or examples.

What is claimed is:

1. A method for preparing a DNA library, comprising the steps of:
    digesting a genomic DNA sample using a restriction endonuclease to obtain a digested product;
    separating the digested product to obtain DNA fragments, wherein the DNA fragments have a length of 200 base pairs (bp) to 700 bp;
    end-repairing the DNA fragments to obtain end-repaired DNA fragments;
    adding a base adenine to the end of the end-repaired DNA fragments to obtain DNA fragments having a terminal base adenine; and
    ligating the DNA fragments having the terminal base adenine with sequencing adaptors to
    obtain the DNA library;

using the DNA library to detect single nucleotide polymorphisms; and wherein the restriction endonuclease is one selected from the group consisting of the following:
(1) Mbo II and Hind III, and
(2) Mbo II and Bcc I.

2. The method according to claim 1, wherein the digested product is separated by means of agarose gel electrophoresis and gel-cutting recovery.

3. The method according to claim 1, further comprising a step of:
sequencing the DNA library to obtain a DNA sequence information.

4. The method according to claim 3, wherein the DNA library is sequenced on a sequencing platform using next generation sequencing (NGS).

* * * * *